United States Patent [19]

Firestone et al.

[11] 3,979,384

[45] Sept. 7, 1976

[54] C-3 SUBSTITUTED CEPHALOSPORINS

[75] Inventors: Raymond A. Firestone, Fanwood; John L. Fahey, Matawan; Burton G. Christensen, Scotch Plains, all of N.J.

[73] Assignee: Merck & Co., Inc., Rahway, N.J.

[22] Filed: Mar. 20, 1975

[21] Appl. No.: 560,660

[52] U.S. Cl. .............................. 260/243 C; 424/246
[51] Int. Cl.² ........................................ C07D 501/24
[58] Field of Search ................................ 260/243 C

[56] References Cited
UNITED STATES PATENTS 3,516,997   6/1970   Takano et al. .................. 260/243 C
3,635,961   1/1972   Butler ............................ 260/243 C

*Primary Examiner*—Nicholas S. Rizzo
*Assistant Examiner*—Jose Tovar
*Attorney, Agent, or Firm*—Walter Patton; Julian S. Levitt; J. Jerome Behan

[57] ABSTRACT

This invention relates to novel organic compounds and to methods for preparing them. More particularly, this invention provides new and useful cephalosporin compounds which are active antibiotics against both gram-positive and gram-negative microorganisms and compounds which are useful intermediates in the preparation of other new cephalosporin compounds.

7 Claims, No Drawings

C-3 SUBSTITUTED CEPHALOSPORINS

The compounds of this invention display an antibacterial action against gram-positive bacteria, for example, *Bacillus subtilis* and *Staphylococcus aureus*, and are also useful against gram-negative bacteria, for example, *Escherichia coli* and *Salmonella schottmuelleri*.

The new and useful cephalosporin compounds of this invention are prepared by the reaction of 7-acylamido-(or 7-acylamido-7-methoxy)-3-formyl-3-cephem-4-carboxylate esters with suitable reagents reactive with the 3-formyl group. The 7-acylamido-(or 7-acylamido-7-methoxy)-3-formyl-3-cephem-4-carboxylic acid esters are prepared from the 7-acylamido-(or 7-acylamido-7-methoxy)-3-cephem-4-carboxylic acid esters presently known in the cephalosporin art by the process described in U.S. Pat. No. 3,351,596.

This invention provides new cephalosporin compounds which may be illustrated by the following general formula:

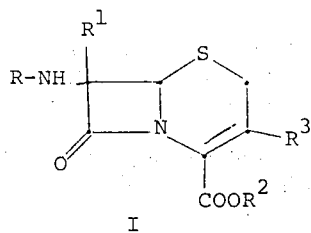

wherein

R may be anyone of the acyl functions presently known in the cephalosporin art, for example, an aliphatic, aromatic, heterocyclic, araliphatic or heterocyclic aliphatic carboxylic acid radical of the formula:

$R^1$ is hydrogen or methoxy;
$R^3$ is a nitrile imine, nitrile oxide, diazomethyl, azomethine imine, azomethine oxide or a five-membered heterocycle.

This invention encompasses the non-toxic pharmaceutical salts of the novel cephalosporins derived from alkali earth metals or tetraalkylammonium salts.

In the case of those compounds wherein the acyl radical is of the formula

$R^{13}$ is hydrogen; halo, such as fluoro, chloro and bromo; amino; lower alkyl amino, wherein the lower alkyl contains 1 to 6 carbon atoms; guanidino; aryl, such as phenyl; substituted aryl, such as halophenyl; phosphono, sulfamino; N-lower alkyl sulfamino, wherein the lower alkyl contains 1 or 2 carbon atoms; hydroxy, (1H)-tetrazolyl, sulfo, carboxy, sulfamyl; N-lower alkyl sulfamyl, wherein the lower alkyl contains from 1 to 2 carbon atoms; and azido.

$R^{14}$ is alkyl containing 1 to 6 carbon atoms; substituted alkyl containing 1 to 6 carbon atoms, wherein the substituent is amino, carboxy; alkene containing 2 to 4 carbon atoms; phenyl; substituted phenyl wherein the substituent is halo, aminomethyl, carboxylmethyl, carboxamidomethyl, hydroxy, nitro, guanidino, guanidinomethyl, methoxy, or methyl; 5-membered monocyclicheterocycle containing one oxygen, one sulfur, one oxygen and two nitrogens, one sulfur and one nitrogen, one sulfur and 2 nitrogens, or 4 nitrogens in the ring such as furyl, thienyl, thiazolyl, isothiazolyl, oxadiazolyl, thiadiazolyl, tetrazolyl and the like; substituted 5-membered monocyclicheterocycle wherein the substituent is nitro, halo, methoxy or methyl; lower alkylthio wherein the lower alkyl contains 1 to 4 carbon atoms, lower alkenethio wherein the alkene contains 1 to 4 carbon atoms, substituted lower alkene thio wherein the substituent is halo; phenylthio, carboxy or cyano.

Especially preferred are those acyl radicals where:
$R^{13}$ is hydrogen, fluoro, amino, methylamino, guanidino, phenyl, chlorophenyl, phosphono, sulfamino, N-methylsulfamino, hydroxy, (1H)-tetrazolyl, sulfo, carboxy, sulfamyl, N-methylsulfamyl and azido;

$R^{14}$ is methyl, n-butyl, n-hexyl, D-(or L)-3-amino-3-carboxypropyl, α-chloro-n-hexyl, 1-butenyl, phenyl, p-hydroxyphenyl, phenoxy, phenylthio, 3- or 4-nitrophenyl, benzyl, 4-guanidinophenoxy, 4-guanidinomethylphenyl, 4-methylaminophenyl, 2,6-dimethoxy-4-guanidinophenyl, chlorophenyl, bromophenyl, aminomethyl, carboxymethyl, carboxamidomethyl, furyl, thienyl, thiazolyl, isothiazolyl, oxadiazolyl, thiadiazolyl, (1H)-tetrazolyl, nitrofuryl, chlorothienyl, methoxythienyl, methylthienyl, methoxythiazolyl, chloroisothiazolyl, methyloxadiazolyl, methylthiadiazolyl, methoxythiadiazolyl; n-butyl mercapto, allymercapto, α-chlorocrotylmercapto.

Examples of these preferred radicals are those wherein R is α-chloro-n-hexylacetyl, allythioacetyl, butylmercaptoacetyl, α-chlorocrotylmercaptoacetyl, caproyl, 1-butenylacetyl, octanoyl, propionyl, 3-phenylpropionyl, β,β-diphenylpropionyl, phenylthioacetyl, D(-)-α-guanidinophenylacetyl, 4-guanidinophenoxyacetyl, 4-guanidinomethylphenylacetyl, 2,6-dimethoxy-4-guanidinophenylacetyl, D-5-amino-5-carboxyvaleryl, phenylacetyl, 3-bromophenylacetyl, p-aminomethylphenylacetyl, 4-carboxymethylphenylacetyl, 4-carboxamidomethylphenylacetyl, 2-furylacetyl, 2-(5-nitro)furylacetyl, 3-furylacetyl, 2-(5-chloro)-thienylacetyl, 2-(5-methoxy)thienylacetyl, α-guanidino-2-thienylacetyl, 3-thienylacetyl, 2-(5-methyl) thienylacetyl, 3-isothiazolyacetyl, 4-(3-methoxy)isothiazolylacetyl, 4-isothiazolyacetyl, 4-(3-methyl)isothiazolyacetyl, 5-isothiazolylacetyl, 4-(3-chloro)-isothiazolyacetyl, 3-methyl-1,2,5-oxadiazol-4-ylacetyl, 1,2,5-thiadiazol-4-ylacetyl, 3-methyl-1,2,5-thiadiazol-4-ylacetyl, 3-chloro-1,2,5-thiadiazol-4-ylacetyl, 3-methoxy-1,2,5-thiadiazol-4-ylacetyl, phenylthioacetyl, 4-pyridylthioacetyl, cyanoacetyl, 1-(1H)-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl, α-sulfophenylacetyl, α-hydroxy-2-thienylacetyl or α-hydroxy-3-thienylacetyl. Especially preferred substituents are D-α-hydroxyphenylacetyl, phenylmalonyl, α-aminoadipoyl, α-aminophenylacetyl and 2-thienylacetyl.

In carrying out the reactions described herein, it is preferred to protect the 4-carboxy group and also other groups in the nucleus which need protection, for example, other carboxy groups, amino groups or hydroxy groups. Maximum yields are obtained by employing these protected compounds. Naturally, the groups which are preferred are those which are easily removed. Examples of these protecting groups, $R^2$ in the formulas, useful for protecting the 4-carboxy group, are trichloroethyl, tertbutyl, benzoylmethyl, p-methoxbenzyl, p-nitrobenzyl, benzyl, benzhydryl, trityl, trimethylsilyl, methoxymethyl and the like. These ester groups may be removed by methods well known to those skilled in the art, for example, the p-nitrobenzyl group may be removed by hydrogenation in the presence of a catalyst such as palladium-on-carbon or by treatment with a strong organic or inorganic acid. A preferred method is treatment with trifluoroacetic acid in the presence of anisole. The tert-butyl, benzhydryl or methoxymethyl groups may also be removed by treatment with strong organic or inorganic acid. Examples of these acids are hydrochloric acid, sulfuric acid, boron trifluoride etherate, formic acid, trifluoroacetic acid, trichloroacetic acid, nitrobenzoic acid and the like.

$R^3$ is a derivative of the 3-formyl group. For example;

$R^3$ is nitrile imine of the formula $-C \equiv N^+-N^--R^4$, wherein $R^4$ is lower alkyl containing 1 to 6 carbon atoms, aryl, arylsulfonyl or substituted arylsulfonyl; nitrile oxide or the formula $-C \equiv N^+-O^-$; diazomethyl of the formula $-C^-H-N^+ \equiv N$; azomethine imine of the formula $-CH=N^+R^5-N^-R^6$, wherein $R^5$ is hydrogen, lower alkyl containing 1 to 6 carbon atoms or aryl and $R^6$ is hydrogen, acyl, or arylalkylcarbonyl and azomethine oxide of the formula $-CH=N^+R^7-O^-$, wherein $R^7$ is lower alkyl containing 1 to 6 carbon atoms atoms or aryl; or $R^3$ is a five-membered heterocycle of the formula:

stituted arylsulfonyl; $R^{11}$ is hydrogen, aryl or lower alkyl containing 1 to 6 carbon atoms; or $R^3$ is a substituted aldoxime of the formula:

$$-\underset{R^{12}}{C}=N-OH$$

or a substituted hydrazonoformyl of the formula:

$$-\underset{R^{12}}{C}=N-NH-R^4$$

wherein $R^4$ is as defined above and $R^{12}$ is SH, SC$_2$H$_5$ or OAc.

Especially preferred compound of this invention are those wherein;

R is α-aminoadipoly, α-aminophenylacetyl, 2-thienylacetyl, phenylmalonyl or α-hydroxyphenylacetyl;

$R^2$ is hydrogen or a protecting group selected from methyl, trichloroethyl, tert-butyl, benzoylmethyl, p-methoxybenzyl, benzyl, benzhydryl or methoxymethyl;

$R^4$ is phenylsulfonyl or p-toluenesulfonyl;

$R^5$ is hydrogen or methyl;

$R^6$ is phenylacetyl;

$R^7$ is methyl;

$R^8$ is hydrogen, lower alkyl containing 1 to 3 carbon atoms, vinyl, methoxy, carbethoxy, carbomethoxy, phenyl, trifluoromethyl or nitrile;

$R^9$ is hydrogen, lower alkyl containing 1 to 3 carbon atoms, vinyl, methoxy, carbethoxy, carbomethoxy, phenyl, trifluoromethyl or nitrile;

$R^{10}$ is hydrogen, phenyl, methyl, phenylacetyl, phenylsulfonyl or p-toluenesulfonyl;

$R^{11}$ is hydrogen, methyl or phenyl, and pharmaceutically acceptable alkali metal or amine salts.

The preferred compounds of this invention are those of formula:

wherein $R^8$ is hydrogen, acyl, lower alkyl containing 1 to 6 carbon atoms, alkenyl, alkoxy, alkoxycarbonyl, aryl, trifluoromethyl or nitrile; $R^9$ is hydrogen, lower alkyl containing 1 to 6 carbon atoms, acyl, alkenyl, alkoxy, alkoxycarbonyl aryl, trifluoromethyl or nitrile; $R^{10}$ is hydrogen, acyl, aryl, lower alkyl containing 1 to 6 carbon atoms, arylalkylcarboxy, arylsulfonyl or subwherein R² and R³ are the following:

| R² | R³ |
|---|---|
| H | 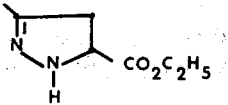 |
| H | 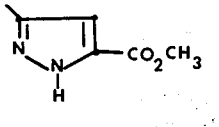 |
| H | 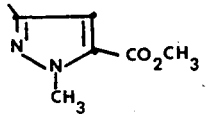 |
| CHPh₂ | 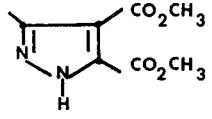 |
| H | 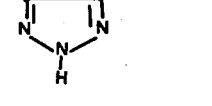 |
| H | 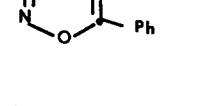 |
| CHPh₂ |  |
| CHPh₂ |  |
| CHPh₂ | 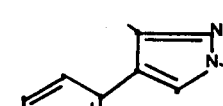 |

-continued

| R² | R³ |
|---|---|
| CHPh₂ |  |
| CHPh₂ | $-\underset{\overset{\|}{\text{NOH}}}{C}-SC_2H_5$ |
| CHPh₂ | $-\underset{\overset{\|}{\text{NOH}}}{C}-SH$ |
| CHPh₂ | $-\underset{\overset{\|}{\text{NOH}}}{C}-\underset{\overset{\|}{O}}{C}-CH_3$ |
| CHPh₂ |  |
| CHPh₂ | $-\underset{\overset{\|}{SH}}{C}=NH-NH-SO_2-\!\!\bigcirc\!\!-CH_3$ |
| CHPh₂ | $-\underset{\overset{\|}{SC_2H_5}}{C}=N-NH-SO_2-\!\!\bigcirc\!\!-CH_3$ |
| CHPh₂ | $\underset{\overset{\|}{OCOCH_3}}{C}=N-\overset{H}{N}-SO_2-\!\!\bigcirc\!\!-CH_3$ | wherein the dashed bond represents the saturated and unsaturated species.

Included in this list of preferred compounds are the salts of the 4-carboxylate group wherein R² is sodium, potassium, ammonium and tri-lower alkyl ammonium wherein the lower alkyl group contains one or two carbon atoms.

The compounds of this invention are prepared by means of a cycloaddition reaction between a 1,3-dipole group at the 3-position of a substituted cephem and a suitable dipolarophile wherein the cephem has the following structure:

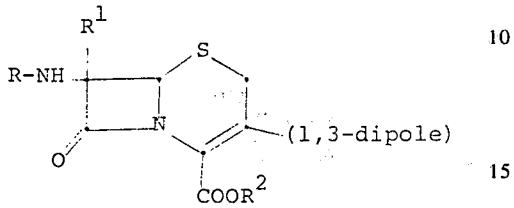

wherein R, $R^1$ and $R^2$ are as defined above and (1,3-dipole) is:

| | |
|---|---|
| $-C \equiv N^+ - N^- - R^4$ | nitrile imine |
| $-C \equiv N^+ - O^-$ | nitrile oxide |
| $-CH^- - N^+ \equiv N$ | diazoalkane |
| $-CH = N^+R^5 - N^- - R^6$ | azomethine imines |
| $-CH = N^+R^7 - O^-$ | azomethine oxides; | wherein $R^4$, $R^5$, $R^6$ and $R^7$ are as defined above. The dipolarophiles have the following structure:

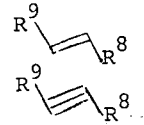

wherein $R^8$ and $R^9$ are as defined above.

The compounds of this invention are prepared according to the following schemes:

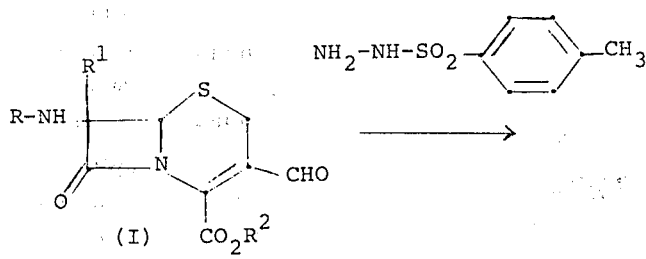

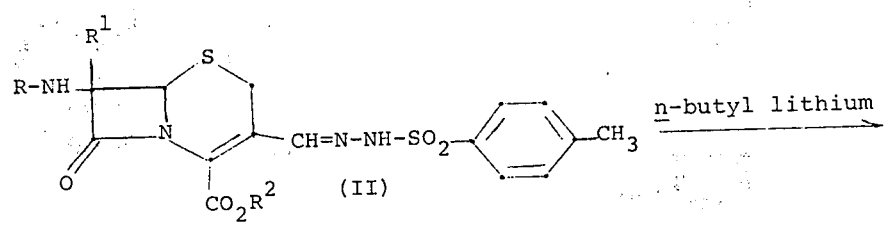

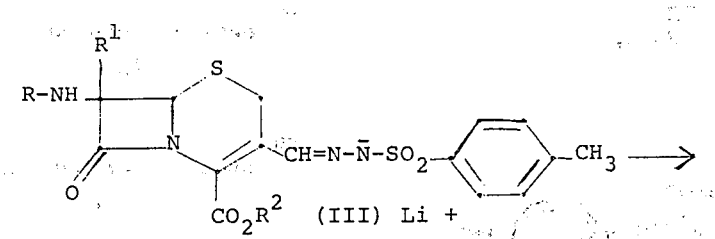

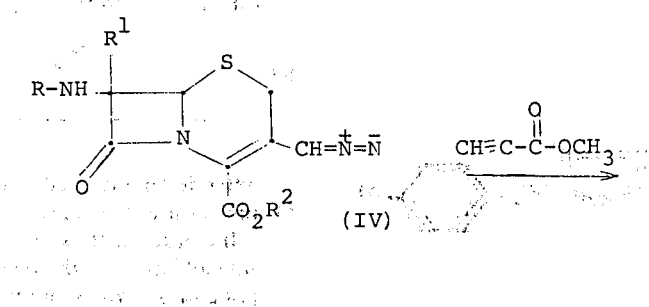

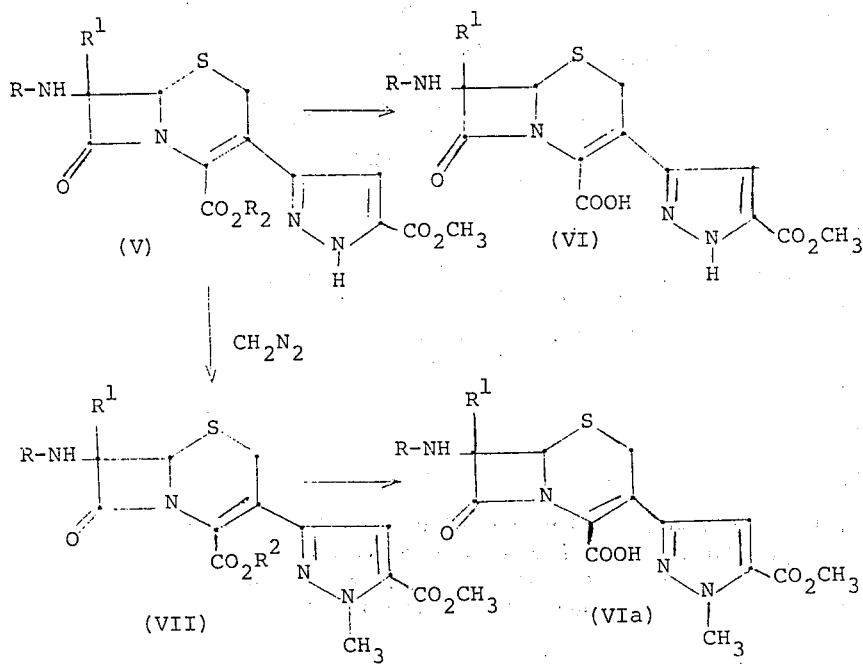

wherein R, R¹ and R² are as defined above.

Central to this scheme is the novel 1,3-dipole; 3-diazomethyl cephem compound, (IV). The 3-diazomethyl compound (IV) is an intermediate in the preparation of other compounds of this invention by reaction with dipolarophiles R⁸—C=C—R⁹ and R⁸≡C—C—R⁹, wherein R⁸ and R⁹ are as defined above. Examples are illustrated by the following scheme:

wherein R, R¹ and R² are as defined above.

The nitrile imines (XI) are prepared by treating (II) with lead tetraacetate according to the following scheme:

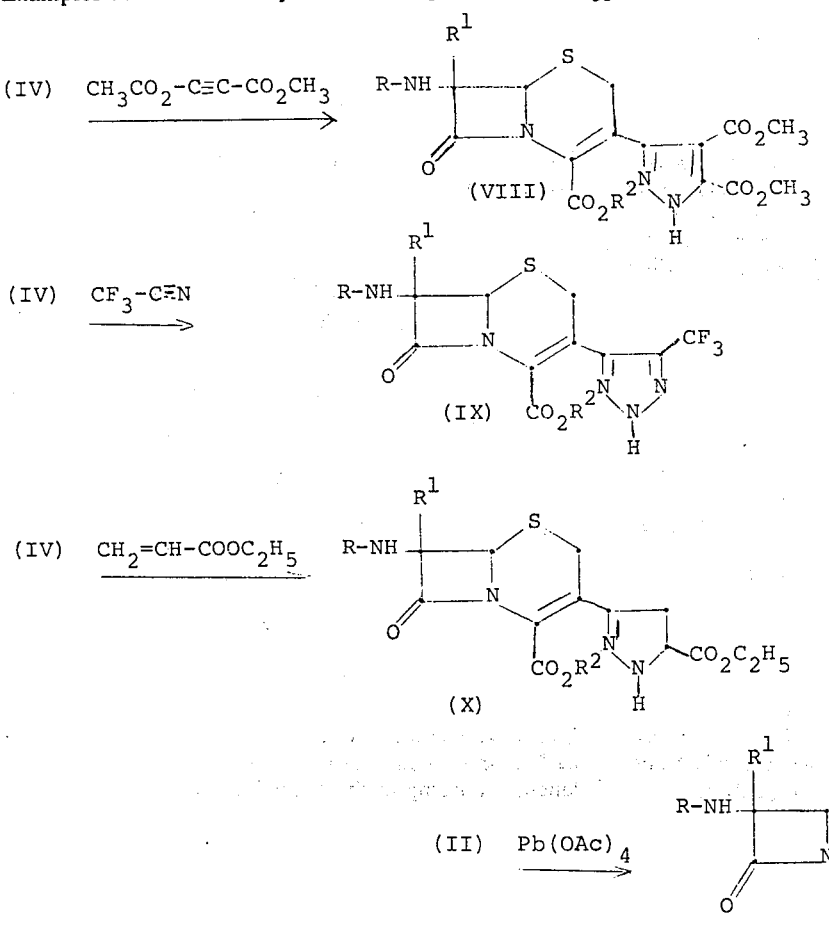

(XIV) 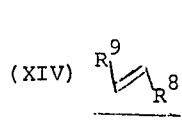

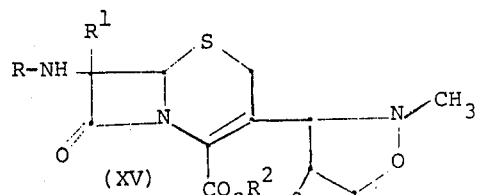

(XIV) 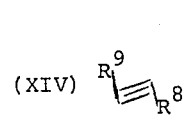

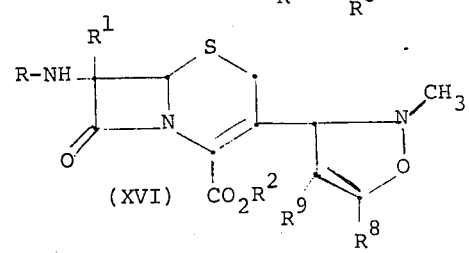

wherein R, R¹ and R² are as defined above. The above 1,3-dipole (XI) is used in situ to react with dipolarophiles, mono- or disubstituted ethylenes or acetylenes, according to the following scheme:

wherein R, R¹, R², R⁸ and R⁹ are as defined above.

The nitrile oxides (XVIII) are prepared by treating the corresponding 3-formyl cephem (I) with hydroxylamine to form the oxime (XVII) which is oxidized with

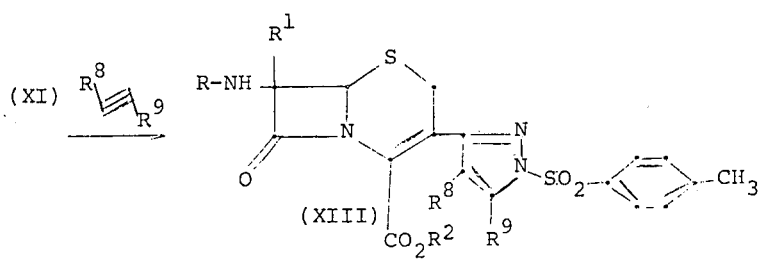

wherein R, R¹, R², R⁸ and R⁹ are as described above.

The cephem compounds having an azomethine oxide in the 3-position (XIV) are prepared from the corresponding 3-formyl cephem (I) by treatment with hydroxyl amine or substituted hydroxyl amine according to the following scheme:

lead tetraacetate to form the nitrile oxide (XVIII) according to the following scheme:

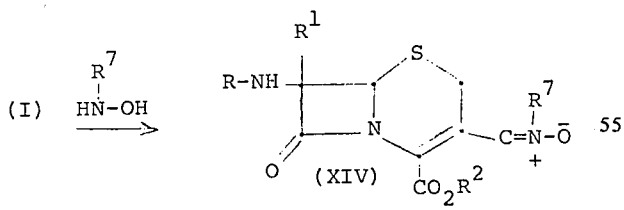

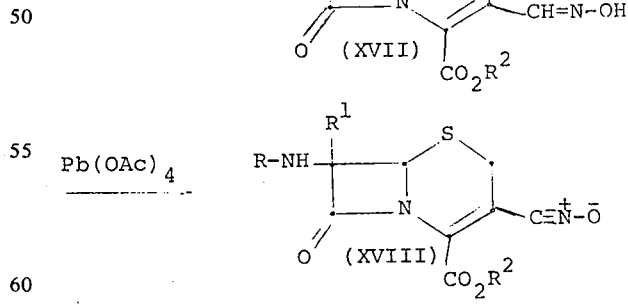

wherein R, R¹, R₂ and R⁷ are as defined above.

The 1,3-dipole, azomethine oxide, (XIV), is reacted with dipolarophiles, mono- or disubstituted ethylenes or acetylenes, according to the following scheme:

The nitrile oxide (XVIII) is reacted with dipolarophiles, mono- and disbustituted ethylenes or acetylenes, according to the following scheme:

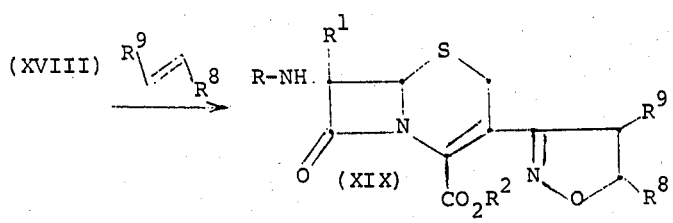

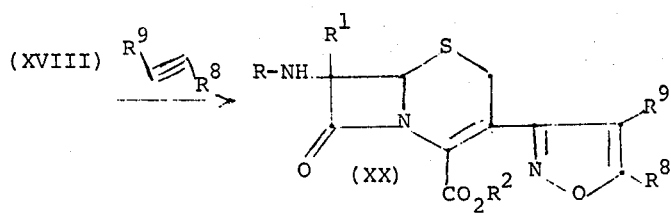

wherein R, $R^1$, $R^2$, $R^8$ and $R^9$ are as defined above.

The azomethine imines (XXI) are prepared by treating the 3-formyl cephem (I) with a substituted hydrazine $R^5NH-NH-R^6$, wherein $R^5$ and $R^6$ are as defined above, according to the following scheme:

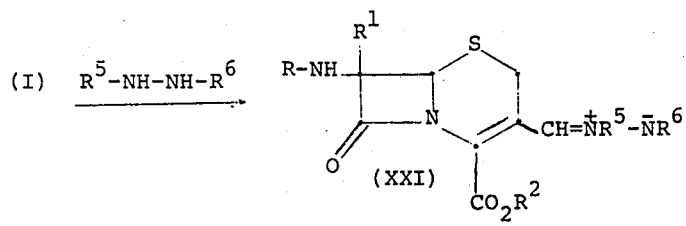

The azomethine imines (XXI) are reacted with dipolarophiles, mono- and disubstituted ethylenes or acetylenes, according to the following scheme:

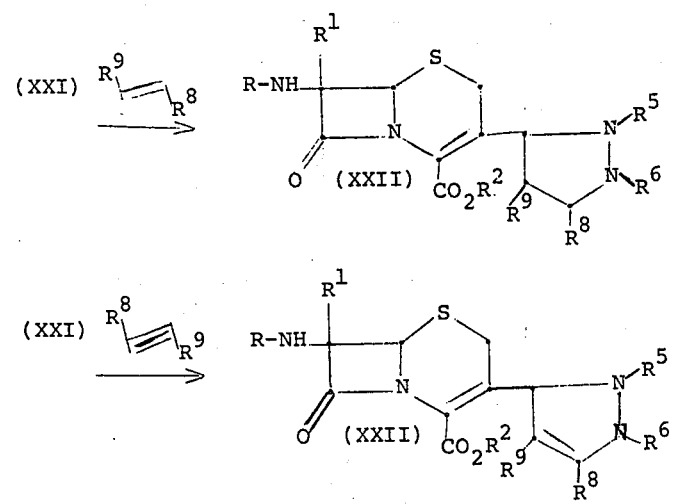

wherein R, $R^1$, $R^2$, $R^5$, $R^6$, $R^8$ and $R^9$ are as defined above.

The compounds of this invention and their salts are valuable antibiotics active against various grampositive and gram-negative bacteria and, accordingly, find utility in human and veterinary medicine. These compounds can therefore be used as antibiotics for treating infections caused by gram-negative bacteria, including *Escherichia coli, Proteus vulgaris, Proteus mirabilis, Proteus morganii, Salmonella schottmuelleri, Klebsiella pneumoniae AD, Klebsiella pneumoniae B*, and *Paracolobactrum arizoniae* and gram-positive bacteria including *Bacillus subtilis, Staphylococcus aureus, Streptococcus pyogenes* and *Diplococcus pneumoniae*. The antibacterial materials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The compounds of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, topically, intravenously or intramuscularly.

The compositions may be presented in a form suitable for treatment of infections in the gastro-intensinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

The compositions are preferably presented in a form suitable for injection. Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form or powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For venterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections.

In the treatment of bacterial infections in man, the compounds of this invention are administered orally or parenterally, in accordance with conventional procedures for antibiotic administration, in an amount of from about 50 to 500 mg./kg. body weight per day and preferably about 150 to 300 mg./kg./day divided in 4 or 6 equal doses administered every 6 or every 4 hours, respectively. They are administered in dosage units containing, for example, 500 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in any given instance will depend upon the type and severity of infection to be treated, and that smaller doses will be employed for pediatric use, all of such adjustments being within the skill of the practitioner in the field.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 – 60%. The composition will generally contain from about 500 mg. to about 1500 mg. by weight of the active ingredient based upon the total weight of the composition; however, in general, it is preferable to employ a dosage amount in the range of from about 750 mg. to 1000 mg. In parenteral administration the unit dosage is usually the pure compound in sterile water solution or in the form of a soluble powder intended for solution. Representative formulations can be prepared by the following procedures:

| Capsules | Per Capsule |
|---|---|
| 3(5-methoxycarbonylpyrazole-3-yl)-7β-(2-thienylacetamido)-ceph-3-em-4-carboxylic acid | 400 mg. |
| Lactose, U.S.P. | 75 mg. |
| (Fill No. 0 Capsules, approx. 475 mg. each) | |

In the above example the active compound and the diluent are mixed to produce a uniform blend, which is then filled into No. 0 hard gelatin capsules, by hand or on a suitable machine, as required.

| Tablets | Per Tablet |
|---|---|
| 3(5-methoxycarbonylpyrazole-3-yl)-7β-(2-thienylacetamido)-ceph-3-em-4-carboxylic acid | 330. mg. |
| Dicalcium phosphate | 192. mg. |
| Lactose, U.S.P. | 190. mg. |
| Cornstarch | 80. mg. |
| Magnesium stearate | 8. mg. |
| | 800. mg. |

In the above example, the active component is blended with the dicalcium phosphate, lactose and about half of the cornstarch. The mixture is granulated with a 15% cornstarch paste and rough-screened. The rough-screened material is screened again through No. 16 screens. The balance of the cornstarch and the magnesium stearate is added and the mixture is compressed into tablets, approximately ½ inch in diameter, each weighing 800 mg.

Alternatively, the active component is blended with the dicalcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ½ inch in diameter, each weighing 800 mg.

| Lyo Form (For Injection) | Per Vial |
|---|---|
| 3(5-methoxycarbonylpyrazole-3-yl)-7$\beta$-(2-thienylacetamido)-ceph-3-em-4-carboxylic acid | 1000 mg. |
| Water-for-Injection, U.S.P. to make | 5 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 5 ml. of sterile water-for-injection is added to the contents of a vial.

| Oral Liquid Forms | Per 1000 ml. |
|---|---|
| 3(5-methoxycarbonylpyrazole-3-yl)-7$\beta$-(2-thienylacetamido)-ceph-3-em-4-carboxylic acid | 500.0 gm. |
| Sucrose | 600.0 gm. |
| Glucose | 250.0 gm. |
| Citric Acid | 13.0 gm. |
| Sodium Benzoate | 1.0 gm. |
| Concentrated Orange Oil | 0.2 ml. |
| Purified water U.S.P. to make | 1000.0 ml. |

The sucrose and glucose are dissolved in about 400 ml. of water using heat to aid solution. This solution is cooled and the citric acid and sodium benzoate, followed by the concentrated orange oil added. The antibiotic is added and the solution brought to 1000 ml. with water. The solution is clarified by filtration through a coarse filter.

Included in this invention are the nontoxic pharmaceutically acceptable salts and esters of the antibiotics.

Such pharmaceutically acceptable salts include the nontoxic metallic salts such as sodium, potassium, calcium and aluminum, the ammonium salt and substituted ammonium salts, e.g. salts of such nontoxic amines as trialklamines, including trimethylamine and triethylamine. Also included within the scope of the present invention are easily hydrolyzed esters which are converted to the free acid form by hydrolysis.

The salts and esters may be prepared according to techniques well known in the art.

For example, metal salts can be prepared by dissolving the antibiotic in water, adding one equivalent of dilute metal base and freeze-drying the solution to provide a dried residue consisting of the antibiotic metal salt.

The examples which follow illustrate the methods by which the products of this invention may be obtained. However, the examples are illustrative only and it should be apparent to one having ordinary skill in the art that this invention includes the functionally equivalent products and methods for their preparation. Therefore, any modification of the processes described herein which results in the formation of an identical product should be construed as constituting an analogous method. The described processes are capable of wide variation and modification and any minor departure or extension is considered as being within the skill of the artisan and as falling within the scope of this invention.

EXAMPLE 1

Preparation of 3-(p-tosylhydrazonoformyl)-7$\beta$-(2-thienylacetamido)-ceph-3-em-4-carboxylate, Sodium Salt A suspension of benzhydryl 3-formyl-7$\beta$-(2-thienylacetamido)-ceph-3-em-4-carboxylate (1.062 g., $2.05 \times 10^{-3}$ mole), p-toluene sulfonyl hydrazide (0.382 g., $2.05 \times 10^{-3}$ mole), and anhydrous magnesium sulfate (3 g.) in chloroform (35 ml.) is stirred under nitrogen at room temperature for 15 minutes then filtered and evaporated in vacuo to give 1.44 g. (100%) of benzhydryl 3-(p-tosylhydrazonoformyl)-7$\beta$-(2-thienylacetamido)-ceph-3-em-4-carboxylate mp 103°–105° (dec.). I.R. (film) 3550, 3300 (NH), 1780 ($\beta$-lactam), 1740 (ester), 1665 (amide) cm$^{-1}$. N.M.R. (CDCl$_3$) $\delta$2.38 (s,3H) 3.58 (dd,2H, J=18Hz), 3.77 (s,2H), 4.90 (d,1H, J=5Hz), 5.87 (dd,1H, J=5Hz, J'=9Hz), 6.70 (d,1H, J'=9Hz), 6.8–8.0 (m, 19H), 8.40 (s,1H)ppm.

The benzhydryl ester (1.44 g.) is dissolved in anisole (1.0 ml.), cooled to 0°C. and trifluoroacetic acid (50.0 ml. at 0°C.) added. The resulting solution is stirred at 0°C. for three minutes and placed under high vacuum to remove the trifluoroacetic acid. After 15 minutes anisole (72.0 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-(p-tosylhydrazonoformyl)-7$\beta$-(2-thienylacetamido)-ceph-3-em-4-carboxylate, sodium salt in 21% yield.

EXAMPLE 2

Preparation of Benzhydryl 3-Diazomethyl-7$\beta$-(2-thienylacetamido)-ceph-3-em-4-carboxylate A solution of benzhydryl 3-(p-tosylhydrazonoformyl)-7β-(2-thienylacetamido)-ceph-3-em-4-carboxylate (343 mg., 5 × 10⁻⁴ mole) in tetrahydrofuran (8 ml.) is stirred at −78° under nitrogen. A solution of n-butyl lithium (2.2M in hexane, 0.23 ml., 5 × 10⁻⁴ mole) is added, the reaction mixture allowed to warm to room temperature, warmed briefly to 40°, filtered, evaporated to an oil and chromatographed on silica gel GF (Uniplate) with chloroform-ethyl acetate (1:1) to give 186 mg. (66%) of benzhydryl 3-diazomethyl-7η-(2-thienylacetamido)-ceph-3-em-4-carboxylate as a pale yellow oil, R$_f$ 0.55. I.R. (film) 3300 (NH), 2100 (CHN$_2$), 1760 (β-lactam, ester), 1670 (amide) cm⁻¹. N.M.R. (CDCl$_3$) δ3.27 (dd,2, J=18Hz), 3.93 (S,2), 4.88 (d,1, J=4Hz), 5.42 (dd,1, J=4Hz, J'=8Hz), 6.50 (S,1), 6.9–7.7 (m,14), 7.82 (d,1, J'=8Hz)ppm.

EXAMPLE 3

Preparation of
3-{3-[5-Carboxyethyl-(pyrazolinyl)]}-7β-(2-thienylacetamido)-ceph-3-em-4-carboxylate, Sodium Salt A solution of benzhydryl 3-diazomethyl-7β-(2-thienylacetamido)-ceph-3-em-4-carboxylate (106 mg., 2.00 × 10⁻⁴ mole), ethyl acrylate (20 μl, 2.0 × 10⁻⁴ mole) and dichloromethane (10 ml.) is stirred under nitrogen at 35°C. for 24 hours. The solvent is removed in vacuo and the resulting oil chromatographed over silica gel GF (Uniplate) with chloroform-ethyl acetate (1:1) to give 46 mg. (36%) of benzhydryl 3-{3-[5-carboxyethyl-(pyrazolinyl)]}-7β-(2-thienylacetamido)-ceph-3-em-4-carboxylate, R$_f$ 0.65. I.R. (film) 3300 (NH), 1780 (β-lactam), 1720 (ester), 1680 (amide, imine) cm⁻¹. N.M.R. (CDCl$_3$) δ1.33 (t,3, J=6Hz), 3.41 (br S,2H), 3.2–4.1 (m,2H), 3.87 (S,2H), 4.30 (q,2H, J=6Hz), 4.97 (d,1H, J=4Hz), 5.84 (dd,1H, J=4Hz, J'=8Hz), 6.67 (d,1H, J=8Hz), 6.8–7.6 (m,16)ppm.

The benzhydryl ester (46 mg.) is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid, 14 mg. (40%). The acid is dissolved in distilled water containing one equivalent of sodium bicarbonate and lyophilized to give 3-{3-[5-carboxyethyl-(pyrazolinyl)]}-7β-(2-thienylacetamido)-ceph-3-em-4-carboxylate, sodium salt.

EXAMPLE 4

Preparation of
3-[3'-(5'-Carboxymethylpyrazolyl)]-7β-(2-thienylacetamido)-ceph-3-em-4-carboxylate, Sodium Salt A solution of benzhydryl 3-diazomethyl-7β-(2-thienylacetamido)-ceph-3-em-4-carboxylate (186 mg., 3.33 × 10⁻⁴ mole), methyl propiolate (28 μl, 3.33 × 10⁻⁴ mole) and chloroform (7 ml.) is stirred under nitrogen at 55°C. for 24 hours. The solvent is removed in vacuo and the oil chromatographed on silica gel 6F (Uniplate) with chloroformethyl acetate (1:1) to give 123 mg. (60%) of benzhydryl 3-3'-(5'-carboxymethylpyrazolyl)]-7β-(2-thienylacetamido)-ceph-3-em-4-carboxylate, mp 188°–189°. I.R. (film) 3300 (NH), 1780 (β-lactam), 1735 (ester), 1705 (ester), 1665 (amide) cm⁻¹. N.M.R. (CDCl$_3$) δ3.67 (dd,2, J=19Hz), 3.87 (S,5), 5.03 (d,1, J=5Hz), 5.90 (dd,1, J=5Hz, J'=8Hz), 6.53 (S,1), 6.7–7.5 (m,16)ppm.

The benzhydryl ester (123 mg.) is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.0 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid, 52 mg. (100%). The acid is dissolved in distilled water containing one equivalent of sodium bicarbonate and lyophilized to give 3-[3'-(5'-carboxymethylpyrazolyl)]-7β-(2-thienylacetamido)-ceph-3-em-4-carboxylate, sodium salt.

EXAMPLE 5

Preparation of
3-[N-Methyl-3'(5'-carboxymethylpyrozolyl)]-7β-(2-thienylacetamido)-ceph-3-em-4-carboxylate, Sodium Salt A solution of benzhydryl 3-[3'(5'-carboxymethylpyrazolyl)]-7β-(2-thienylacetamido)-ceph-3-em-4-carboxylate (50 mg., 0.814 × 10⁻⁴ mole) and dichloromethane (10 mls.) was added to excess diazomethane in ether and stirred at room temperature under nitrogen for three hours. Removal of the solvent in vacuo gave 51 mg. (100%) of benzhydryl 3-[N-methyl-3'(5'-carboxymethylpyrazolyl)]-7β-(2-thienylacetamido)-ceph-3-em-4-carboxylate, mp 206°–208°. Mass spectromitry showed a peak at m⁺ 628. I.R. (film) 3320 (NH), 1790 (β-lactam), 1755 (ester), 1675 (amide) cm⁻¹. N.M.R. (CDCl$_3$)δ3.74 (dd,2, J=19Hz), 3.80 (S,2), 3.87 (S,6), 5.03 (d,1, J=5Hz), 5.90 (dd,1, J=5Hz, J'=8Hz), 6.47 (d,1, J'=8Hz) 6.54 (S,1), 7.0–7.5 (m,14)ppm.

The benzhydryl ester (51 mg.) is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.0 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The choroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid, 24 mg. (64%). The acid is dissolved in distilled water containing one equivalent of sodium bicarbonate and lyophilized to give 3-[N-methyl-3'(5'-carboxymethylpyrozolyl)]-7$\beta$-(2-thienylacetamido)-ceph-3-em-4-carboxylate, sodium salt.

EXAMPLE 6

Preparation of Benzhydryl 3-[3'(4',5'-Dicarboxymethylpyrazolyl)]-7$\beta$-(2-thienylacetamido)-ceph-3-em-4-carboxylate A solution of benzyhydryl 3-diazomethyl-7$\beta$-(2-thienylacetamido)-ceph-3-em-4-carboxylate (42 mg., 8 $\times$ 10$^{-5}$ mole) and dichloromethane (4ml.) is stirred with dimethyl acetylene dicarboxylate (12.4 $\mu$l, 8.0 $\times$ 10$^{-5}$ mole) at room temperature under nitrogen for one hour. The solvent is removed in vacuo and the oil chromatographed on silica gel GF (Uniplate) with chloroform-ethyl acetate (1:1) to give 20 mg. (36%) of benzhydryl 3-[3'(4',5'-dicarboxymethyl pyrazolyl)]-7$\beta$-(2-thienylacetamido)-ceph-3-em-4-carboxylate. Mass spectra showed a peak at M$^+$700. I.R. (film) 3400 (NH), 1790 ($\beta$-lactam), 1750 (ester), 1690 (amide) cm$^{-1}$.

EXAMPLE 7

Preparation of 7$\beta$-(2-Thienylacetamido)-3-[5-(4-trifluoromethyl-2,1,3-triazolyl)]-ceph-3-em-4-carboxylate, Sodium Salt A solution of benzhydryl 3-diazomethyl-7$\beta$-(2-thienylacetamido)-ceph-3-em-4-carboxylate (106 mg., 2 $\times$ 10$^{-4}$ mole) and acetonitrile (50 ml.) is stirred at room temperture under nitrogen while a slow stream of trifluoroacetonitrile is bubbled in for five days. The solvent is removed in vacuo to give benzhydryl 7$\beta$-(2-thienylacetamido)-3-[5-(4-trifluoromethyl-2,1,3-triazolyl)]-ceph-3-em-4-carboxylate. I.R. (film 3330 (NH), 1780 ($\beta$-lactam), 1750 (ester), 1670 (amide) cm$^{-1}$.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid, 4 mg. (5%). The acid is dissolved in distilled water containing one equivalent of sodium bicarbonate and lyophilized to give 7$\beta$-(2-thienylacetamido)-3-[5-(4-trifluoromethyl-2,1,3-triazolyl)]-ceph-3-em-4-carboxylate, sodium salt.

EXAMPLE 8

Preparation of 3-Aldoxime-7$\beta$-(2-thienylacetamido)-ceph-3-em-4-carboxylate, Sodium Salt A suspension of benzhydryl 3-formyl-7$\beta$-(2-thienylacetamido)-ceph-3-em-4-carboxylate (414 mg., 8 $\times$ 10$^{-4}$ mole), powdered hydroxylamine hydrochloride (116 mg., 16 $\times$ 10$^{-4}$ mole) and 2-propanol (25 ml.) is stirred under nitrogen until solution occurred. The resulting solution is evaporated in vacuo, and partitioned between dichloromethane and water. The organic layer is washed with aqueous sodium chloride, dried and evaporated to an oil that is chromatographed on silica gel GF (Uniplate) with chloroform-ethyl acetate (5:1) to give 124 mg. (29%) of benzhydryl 3-aldoxime-7$\beta$-(2-thienylacetamido)-ceph-3-em-4-carboxylate, mp 190°–191° (dec.). I.R. (film) 3300 (OH, NH), 1780 ($\beta$-lactam), 1735 (ester), 1670 (amide) cm$^{-1}$. N.M.R. (CDCl$_3$) $\delta$3.72 (dd,2, J=18Hz), 3,80 (S,2), 4.96 (d,1, J=5Hz), 5.90 (dd,1, J=5Hz, J'=8Hz), 6.73 (d,1, J'=8Hz), 7.2–7.6 (m,15), 8.40 (S,1)ppm.

The benzhydryl ester (124 mg.) is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjsuted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid, 19 mg. (45%). The acid is dissolved in distilled water containing one equivalent of sodium bicarbonate and lyophilized to give 3-alkoxime-7$\beta$-(2-thienylacetamido)-ceph-3-em-4-carboxylate, sodium salt.

EXAMPLE 9

Preparation of 3-Nitrileoxide-7$\beta$-(2-thienylacetamido)-ceph-3-em-4-carboxylate, Benzhydryl Ester A mixture of benzhydryl 3-aldoxime-7$\beta$-(2-thienylacetamido)-ceph-3-em-4-carboxylate (319.8 mg., 6.00 $\times$ 10$^{-4}$ mole) and dichloromethane (50 ml.) is stirred at −78°C. under nitrogen while triethylamine (200 $\mu$l, 3.0 $\times$ 10$^{-3}$ mole is added). After 5 minutes a solution of lead tetraacetate (320 mg., 6.6 $\times$ 10$^{-4}$ mole) and dichloromethane (10 ml.) is added dropwise. The reaction mixture is allowed to warm to 0°C., poured into a 10% aqueous sodium chloride solution and extracted with ether (3 × 60 ml.). The ether extract is dried over MgSO$_4$, filtered and evaporated in vacuo to give a pale yellow oil that is immediately chromatographed over silica gel with benzene: THF (10:2) to give benzhydryl 3-nitrileoxide-7β(2-thienylacetamido)-ceph-3-em-4-carboxylate, 102 mg. (33%). I.R. (film) 3220, 2285, 1790, 1730, 1675 cm$^{-1}$; N.M.R. (CDCl$_3$)δ3.38 (d,1H, J=7Hz), 3,78 (S,2H), 4.02 (d,1H, J=7Hz), 4.92 (d,1H, J=5Hz), 6.0 (dd, 1H, J=5Hz, J'=8Hz), 6.9–7.6 (m,15H)ppm.

EXAMPLE 10

Preparation of
3-(5-Phenyloxazol-3-yl)-7β-(2-thienylacetamido)-ceph-3-em-4-carboxylate, Sodium Salt A solution of benzhydryl 3-nitrileoxide-7β(2-thienylacetamido)-ceph-3-em-4-carboxylate (318 mg. 6.00 × 10$^{-4}$ mole) and phenyl acetylene (2 ml.) is stirred at room temperature under nitrogen for 30 minutes. The solvent is removed in vacuo to give a pale yellow oil that is chromatographed over silica gel with benzene: THF (10:2) to give benzhydryl 3(5-phenyloxazolyl)-7β(2-thienylacetamido)-ceph-3-em-4-carboxylate, 36 mg. (9.5%). I.R. (film) 3300, 1790, 1740, 1675 cm$^{-1}$; N.M.R. (CDCl$_3$)δ3.18 (d,1H, J=18Hz), 3.80 (S,2H), 3.97 (d,1H, J=18Hz), 4.97 (d,1H, J=5Hz), 5.95 (dd,1H, J=5Hz, J'=8Hz), 6.54 (d,1H, J=1Hz), 6.9–7.6 (m,20H)ppm. The ester is cleaned with PhOCH$_3$:TFA (5:1) at 0° for 3 minutes followed by conversion to the sodium salt in 100% yield by treatment with sodium bicarbonate. Preparation of the methyl ester with diazomethane gave a product with a peak at m$^+$ 841 in mass spectrometry.

EXAMPLE 11

Preparation of
3-(4',5'-Dihydro-5-cyano-oxazol-3-yl)-7β(2-thienylacetamido)-ceph-3-em-4-carboxylate, Benzhydryl Ester A solution of benzhydryl 3-nitrileoxide-7β(2-thienylacetamido)-ceph-3-em-4-carboxylate (106.2 mg., 2.0 × 10$^{-4}$ mole) and acrylonitrile (2ml.) is stirred for 10 minutes. The solvent was removed to give an oil that was chromatographed over silica gel with chloroform:ethyl acetate (10:2) to give 2 mg. (2%) benzhydryl 3(4',5'-dihydro-5-cyano-oxazol-3-yl)-7β(2-thienylacetamido)-ceph-3-em-4-carboxylate, R$_f$=0.65. I.R. (film) 3250, 1790, 1740, 1670 cm$^{-1}$; m/e 404, 180, 167.

EXAMPLE 12

Preparation of Benzhydryl
3-Nitriletosylimine-7β-(2-thienylacetamido)-ceph-3-em-4-carboxylate A solution of benzhydryl 3-tosylhydrazono-7β-(2-thienylacetamido)-ceph-3-em-4-carboxylate (137 mg. 2.0 × 10$^{-4}$ mole) in dichloromethane (15 ml.) is stirred at −75°C. while triethylamine (70 μl, 10 × 10$^{-4}$ mole) is added. After five minutes a solution of lead tetraacetate (107 mg., 2.2 × 10$^{-4}$ mole) in dichloromethane (10 ml.) is added dropwise. The resulting solution is allowed to warm to 0°C. washed rapidly with saturated NaCl solution and evaporated in vacuo to give benzhydryl 3-nitriletosylimine-7β-(2-thienylacetamido)-ceph-3-em-4-carboxylate. I.R. (film) 3300, 2080, 1780, 1720, 1665 cm$^{-1}$.

EXAMPLE 13

Preparation of
3-{3'-[N$^1$-Tosyl-5'-phenyl-(pyrazolinyl)]}-7β-(2-thienylacetamido)-ceph-3-em-4-carboxylate Sodium Salt A solution of benzhydryl 3-tosylhydrazano-7β-(2-thienylacetamido)-ceph-3-em-4-carboxylate (137 mg., 2.0 × 10$^{-4}$ mole) and (6 × 10$^{-4}$ mole) of styrene in 25 ml. dichloromethane is stirred at −75°C. while triethylamine (70 μl, 10 × 10$^{-4}$ mole) is added. After five minutes a solution of lead tetraacetate (107 mg., 2.2 × 10$^{-4}$ mole) in 10 ml. dichloromethane is added dropwise. The resulting solution is allowed to warm to 0°C., washed with saturated NaCl solution and evaporated in vacuo to give benzhydryl 3-{3-[N$^1$-tosyl-4-phenyl-(pyrazolinyl)]}-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-{3-[N$^1$-tosyl-4-phenyl-(pyrazolinyl)]}-7β-(2-thienylacetamido)-ceph-3-em-4-carboxylate, sodium salt.

EXAMPLE 14

Preparation of
3-{3'-[N$^1$-Tosyl-4'-phenyl-(pyrazolyl)]}-7β-(2-thienylacetamido)-ceph-3-em-4-carboxylate, Sodium Salt The above-named compound is prepared by the process described in Example 13 wherein an equimolar amount of phenylacetylene is substituted for styrene.

EXAMPLE 15

Preparation of Benzhydryl
3-Methylnitrone-7β-(2-thienylacetamido)-ceph-3-em-4-carboxylate A solution of benzhydryl 3-formyl-7β-(2-thienylacetamido)-ceph-3-em-4-carboxylate (137 mg. 2.0 × 10$^{-4}$ mole), N-methylhydroxylamine (28.2 mg., 6.0 × 10$^{-4}$ mole) and 2-propanol (5 ml.) is refluxed for 30 minutes. Evaporation of the solvent and chromatography over silica gel with 4:1 chloroform:ethyl acetate gives benzhydryl 3-methylnitrone-7β-(2-thienylacetamido)-ceph-3-em-4-carboxyl.

EXAMPLE 16

Preparation of
3-(2',3',4',5'-Tetrahydro-N-methy-5'-phenyl-oxazol- 3-yl)-7β-(2-thienylacetamido)-ceph-3-em-4-carboxylate, Sodium Salt A solution of benzhydryl 3-methylnitrone-7β-(2-thienylacetamido)-ceph-3-em-4-carboxylate (2.0 × $10^{-4}$ mole), prepared by the method described in Example 15, and styrene (2 ml.) is stirred for two minutes. The solvent is removed in vacuo to give benzhydryl 3-(2',3',4',5'-tetrahydro-5-phenyl-oxazol-3-yl)-7β-(2-thienylacetamido)-ceph-3-em-4-carboxylate which is chromatographed over silica gel with chloroform:ethyl acetate (10:2).

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum souce and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaported to give the free acid. The acid is dissolved in distilled water containing one equivalent of sodium bicarbonate nd lyophilized to give 3-(2',3',4',5'-tetrahydro-N-methyl-5-phenyloxazol-3-yl)-7β-(2-thienylacetamido)-ceph-3-em-4-carboxylate, sodium salt.

EXAMPLE 17

Preparation of 3-(4',5'-Dihydro-N-methyl-5-phenyl-oxazol-3-yl)-7β-(2-thienylacetamido)-ceph-3-em-4-carboxylate, Sodium Salt The above-named compound is prepared by the process described in Example 16 wherein an equivalent amount of phenylacetylene is substituted for styrene.

EXAMPLE 18

Preparation of 3-(C-Ethylthioaldoxime)-7β-(2-thienylacetamido)-ceph-3-em-4-carboxylate, Sodium Salt A solution of benzhydryl 3-nitrileoxide-7β-(2-thienylacetamido-ceph-3-em-4-carboxylate (480 mg., 9.0 × $10^{-4}$ mole), prepared by the process described in Example 9, and ethanethiol (5 ml.) is stirred at room temperature for 15 minutes. The excess ethanethiol is removed in vacuo and the foamy residue chromatographed over silica gel with chloroform:acetone (10:1) to give 3-(C-ethylthioxime-7β-(2-thienylacetamido)-ceph-3-em-4-carboxylate. MP 103°–106°, I.R. 3300, 1780, 1720, 1665 cm$^{-1}$.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-(C-ethylthioaldoxime)-7β-(2-thienylacetamido)-ceph-3-em-4-carboxylate, sodium salt.

EXAMPLE 19

Preparation of 3-(C-sulfhydrylaldoxime)-7β-(2-thienylacetamido)-ceph-3-em-4-carboxylate, Sodium Salt A solution of benzhydryl 3-nitrileoxide-7β-(2-thienylacetamido)-ceph-3-em-4-carboxylate (480 mg., 9.0 × $10^{-4}$ mole), prepared by the process described in Example 9, in 5 ml. dichloromethane solvent is stirred at room temperature for 15 minutes while a slow stream of hydrogen sulfide gas is bubbled in. The excess gas and solvent is removed in vacuo and the residue chromatographed over silica gel with chloroform:acetone (10:1) to give benzhydryl 3-(C-sulfhydrylaldoxime)-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-(C-sulfhydrylaldoxime)-7β-(2-thienylacetamido)-ceph-3-em-4-carboxylate, sodium salt.

EXAMPLE 20

Preparation of 3-(C-Acetoxyaldoxime)7β-(2-thienylacetamido)-ceph-3-em-4-carboxylate, Sodium Salt The above-named compound is prepared by the process described in Example 18 wherein an equivalent amount of acetic acid is substituted for ethanethiol.

EXAMPLE 21

Preparation of Benzhydryl
7β-(2-thienylacetamido)-3-[3-(1-phenylacetyl)-2-methyl-5-phenyltetrahydropyrazoly]-decephalosporanate, Sodium Salt A solution of benzhydryl 3-formyl-7β-(2-thienylacetamido)-ceph-3-em-4-carboxylate ($1 \times 10^{-3}$ mole) and N-phenylacetyl-N'-methyl hydrazine is refluxed together in 25 ml. toluene for ½ hour in the presence of styrene ($3 \times 10^{-3}$ mole). The 1,3-dipole, C-[benzhydryl-7β-(2-thienylacetamido)3-decephalosporanyl]-N-methyl-N'-phenylacetyl azomethine imine, is formed and reacts in situ with the dipolarophile, styrene. After evaporation of the solvent, the residue is chromatographed on silica gel with 4:1 chloroform::ethyl acetate to afford benzhydryl 7β-(2-thienylacetamido)-3-[3-(1-phenylacetyl)-2-methyl-5-phenyltetrahydropyrazolyl]decephalosporanate.

The benzhydryl ester is dissolved in anisole (1.0 l.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give benzhydryl 7β-(2-thienylacetamido)-3-[3-(1-phenylacetyl)-2-methyl-5-phenyltetrahydropyrazolyl]-decephalosporanate, sodium salt.

EXAMPLE 22

Preparation of Benzhydryl
3-[3-(1-Phenylacetyl)-2-methyl-5-phenyl-2,3-dihydropyrazolyl]decephalosporanate, Sodium Salt The above-named compound is prepared by the process described in Example 21 wherein an equivalent amount of phenylacetylene is substituted for styrene.

EXAMPLE 23

Preparation of
3-Mercaptomethyl-7β-(2-thienylacetamido)-ceph-3-em-4-carboxylate, Sodium Salt A solution of benzhydryl 3-diazomethyl-7β-(2-thienylacetamido)-ceph-3-em-4-carboxylate ($9.0 \times 10^{-4}$ mole), prepared by the process described in Example 2, in 5 ml. dichloromethane solvent is stirred at room temperature while a slow stream of hydrogen sulfide gas is bubbled in. The excess gas and solvent is removed in vacuo and the residue chromatographed over silica gel with chloroform:acetone (10:1) to give benzhydryl 3-mercaptomethyl-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-mercaptomethyl-7β-(2-thienylacetamido)-ceph-3-em-4-carboxylate, sodium salt.

EXAMPLE 24

Preparation of
3-ethylthiomethyl-7β-(2-thienylacetamido)-ceph-3-em-4-carboxylate, Sodium Salt A solution of benzhydryl 3-diazomethyl-7β-(2-thienylacetamido)-ceph-3-em-4-carboxylate ($9.0 \times 10^{-4}$ mole), prepared by the process described in Example 2, and ethanethiol (5 ml.) is stirred at room temperature for 15 minutes. The excess ethanethiol is removed in vacuo and the residue chromatographed over silica gel with chloroform:acetone (10:1) to give benzhydryl 3-ethylthiomethyl-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-ethylthiomethyl-7β-(2-thienylacetamido)-ceph-3-em-4-carboxylate, sodium salt.

EXAMPLE 25

Preparation of
3-Acetoxymethyl-7β-(2-thienylacetamido)-ceph-3-em-4-carboxylate, Sodium Salt The above-named compound is prepared by the process described in Example 24 wherein an equivalent amount of acetic acid is substituted in place of ethanethiol.

EXAMPLE 26

Preparation of
3-(C-Sulfhydryltosylhydrazonoformyl)-7β-(2-thienylacetamido)-ceph-3-em-4-carboxylate, Sodium Salt A solution of benzhydryl 3-nitriletosylimine-7β-(2-thienylacetamido)-ceph-3-em-4-carboxylate (9.0 × 10$^{-4}$ mole), prepared by the process described in Example 12, in 5 ml. dichloromethane solvent is stirred at room temperature while a slow stream of hydrogen sulfide gas is bubbled in. The excess gas and solvent is removed in vacuo and the residue chromatographed over silica gel with chloroform:acetone (10:1) to give benzyhydryl 3-(C-sulfhydryltosylhydrazonoformyl)-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-(C-sulfhydryltosylhydrazonoformyl)-7β-(2-thienylacetamido)-ceph-3-em-4-carboxylate, sodium salt.

EXAMPLE 27

Preparation of
3-(C-Ethylthiotosylhydrazonoformyl)-7β-(2-thienylacetamido)-ceph-3-em-4-carboxylate, Sodium Salt A solution of benzhydryl 3-nitriletosylimine-7β-(2-thienylacetamido)-ceph-3-em-4-carboxylate (9.0 × 10$^{-4}$ mole), prepared by the process described in Example 12, and ethanethiol (5 ml.) is stirred at room temperature for 15 minutes. The excess ethanethiol is removed in vacuo and the residue chromatographed over silica gel with chloroform:acetone (10:1) to give benzhydryl 3-(C-ethylthiotosylhydrazonoformyl)-7β-(2-thienylacetamido)-ceph-3-em-4-carboxylate.

The benzhydryl ester is dissolved in anisole (1.0 ml.), cooled to 0°C. and trifluoroacetic acid (5.0 ml. at 0°C.) added. The resulting solution is stirred at 0°C. for three minutes and placed under high vacuum to remove the trifluoroacetic acid. After 15 minutes anisole (7.2 ml.) is added and high vacuum resumed while the solution is allowed to warm to room temperature. After 20 minutes it is briefly warmed to 35°C., removed from the vacuum source and transferred to a separating funnel with the aid of 400 ml. chloroform. The chloroform layer is overlaid with water which was adjusted to pH 8.5 with sodium bicarbonate. This alkaline layer is washed three times with chloroform, overlaid with ethyl acetate, adjusted to pH 2.5 with phosphate buffer and extracted with ethyl acetate. The combined ethyl acetate layers are dried over anhydrous magnesium sulfate, filtered and evaporated to give the free acid. The acid is dissolved in distilled water containing one equivalent of sodium bicarbonate and lyophilized to give 3-(C-ethylthiotosylhydrazonoformyl)-7β-(2-thienylacetamido)-ceph-3-em-4-carboxylate, sodium salt.

EXAMPLE 28

Preparation of
3-(C-Acetoxytosylhydrazonoformyl)-7β-(2-thienylacetamido)-ceph-3-em-4-carboxylate, Sodium Salt The above-named compound is prepared by the process described in Example 27 wherein an equivalent amount of acetic acid is substituted in place of ethanethiol.

What is claimed is:
1. A compound of the formula:

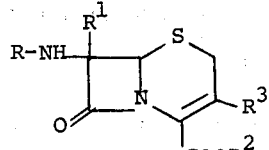

wherein
R is an acyl radical of the formula

wherein
R$^{13}$ is hydrogen; halo selected from the group consisting of fluoro, chloro and bromo; amino; lower alkyl amino, wherein the lower alkyl has 1 to 6 carbon atoms; guanidino; phenyl; halophenyl; phosphono; sulfamino; N-lower alkyl sulfamino wherein the lower alkyl has 1 or 2 carbon atoms; hydroxy; (1H)-tetrazolyl; sulfo; carboxy; sulfamyl; N-lower alkyl sulfamyl wherein the lower alkyl contains from 1 to 2 carbon atoms; and azide;

R$^{14}$ is alkyl having 1 to 6 carbon atoms; substituted alkyl having 1 to 6 carbon atoms, wherein the substituent is amino; carboxy; alkene having 2 to 4 carbon atoms; phenyl; substituted phenyl wherein the substituent is halo, aminomethyl, carboxylmethyl, carboamidomethyl, hydroxy, nitro, guanidino, guanidinomethyl, methoxy, or methyl; 5-membered monocyclicheterocycle having one oxygen, one sulfur, one oxygen and two nitrogens, one sulfur and one nitrogen, one sulfur and two nitrogens, or four nitrogens in the ring selected from the group consisting of furyl, thienyl, thiazolyl, isothiazolyl, oxadiazolyl, thiadiazolyl and tetrazolyl; substituted 5-membered monocyclicheterocycle wherein the substituent is nitro, halo, methoxy or methyl; lower alkylthio wherein the lower alkyl has 1 to 4 carbon atoms; lower alkenethio wherein the alkene has 1 to 4 carbon atoms; substituted lower alkene thio wherein the substituent is halo; phenylthio; carboxy or cyano;

R$^1$ is hydrogen or methoxy;

R$^2$ is hydrogen or a protecting group selected from methyl, trichloroethyl, tert-butyl, benzoylmethyl, p-methoxybenzyl, benzyl, benzhydryl, methoxymethyl or a pharmaceutically acceptable salt;

$R^3$ is selected from the group consisting of nitrile imine of the formula $-C\equiv N^+-N^--R^4$, wherein $R^4$ is lower alkyl having 1 to 6 carbon atoms, phenylsufonyl, p-toluenesulfonyl; nitrile oxide of the formula $-C\equiv N^+-O^-$; diazomethyl of the formula $-CH^--N^+\equiv N$; azomethine imine of the formula $-CH=NR^{+5}-NR^{-6}$, wherein $R^5$ is hydrogen, lower alkyl having 1 to 6 carbon atoms and $R^6$ is hydrogen, phenylacetyl and azomethine oxide of the formula $-CH=NR^{+7}-O,^-$ wherein $R^7$ is lower alkyl having 1 to 6 carbon atoms.

2. A compound according to claim 1 wherein
R is α-aminoadipoyl, α-aminophenylacetyl, 2-thienylacetyl, phenylmalonyl or α-hydroxyphenylacetyl;
$R^2$ is hydrogen or a protecting group selected from methyl, trichloroethyl, tert-butyl, benzoylmethyl, p-methoxybenzyl, benzyl, benzhydryl, methoxymethyl or a pharmaceutically acceptable alkali metal salt;
$R^4$ is phenylsulfonyl or p-toluenesulfonyl;
$R^5$ is hydrogen or methyl;
$R^6$ is phenylacetyl;
$R^7$ is methyl.

3. A compound according to claim 2 wherein
R is 2-thienylacetyl;
$R^1$ is hydrogen or methoxy;
$R^2$ is benzhydryl or sodium;
$R^4$ is p-toluenesulfonyl.

4. A compound according to claim 2 wherein
R is 2-thienylacetyl;
$R^1$ is hydrogen or methoxy;
$R^2$ is benzylhydryl or sodium salt;
$R^3$ is nitrile oxide.

5. A compound according to claim 2 wherein
R is 2-thienylacetyl;
$R^1$ is hydrogen or methoxy;
$R^2$ is benzhydryl or sodium salt;
$R^3$ is diazomethyl.

6. A compound according to claim 2 wherein
R is 2-thienylacetyl;
$R^1$ is hydrogen or methoxy;
$R^2$ is benzyhydryl or sodium salt;
$R^3$ is azomethine imine of the formula $-CH=N-R^5-N^--R^6$ wherein
$R^5$ is methyl and
$R^6$ is phenylacetyl.

7. A compound according to claim 2 wherein
R is 2-thienylacetyl;
$R^1$ is hydrogen or methoxy;
$R^2$ is benzhydryl or sodium salt;
$R^3$ is azomethine oxide of the formula $-CH=NR^{+7}-O^-$ wherein
$R^7$ is methyl.

* * * * *

UNITED STATES PATENT OFFICE
CERTIFICATE OF CORRECTION

PATENT NO. : 3,979,384
DATED : September 7, 1976
INVENTOR(S) : Raymond A. Firestone, John L. Fahey and Burton G. Christensen It is certified that error appears in the above-identified patent and that said Letters Patent are hereby corrected as shown below:

At Col. 30, line 43, delete "contains" and insert ---has ---.

At Col. 30, line 50, delete "carboamidomethyl" and insert ---carboxamidomethyl---.

Signed and Sealed this

Seventh Day of December 1976

[SEAL]

Attest:

RUTH C. MASON
Attesting Officer

C. MARSHALL DANN
Commissioner of Patents and Trademarks